United States Patent [19]
Hofmann et al.

[11] Patent Number: 5,258,035
[45] Date of Patent: Nov. 2, 1993

[54] FEMORAL PROSTHESIS WITH WEDGE HAVING OPPOSED TAPERS

[75] Inventors: Aaron A. Hofmann, Salt Lake City, Utah; James E. Williams, Austin, Tex.

[73] Assignee: Intermedics Orthopedics, Inc., Austin, Tex.

[21] Appl. No.: 889,823

[22] Filed: May 29, 1992

[51] Int. Cl.$^5$ ............................................. A61F 2/36
[52] U.S. Cl. ........................................ 623/23; 623/18
[58] Field of Search ...................... 623/16, 18, 19, 20, 623/22, 23

[56] References Cited

U.S. PATENT DOCUMENTS

| | | | |
|---|---|---|---|
| 3,466,670 | 9/1969 | Christiansen | 623/23 |
| 4,404,693 | 9/1983 | Zweymuller | 623/23 |
| 4,608,053 | 8/1986 | Keller | 623/23 |
| 4,645,506 | 2/1987 | Link | 623/23 |
| 4,718,916 | 1/1988 | Morscher | 623/23 |
| 4,904,269 | 2/1990 | Elloy et al. | 623/23 |
| 4,911,722 | 3/1990 | Crespy | 623/23 |
| 4,936,863 | 6/1990 | Hofmann | 623/23 |

FOREIGN PATENT DOCUMENTS

| | | | |
|---|---|---|---|
| 0050533 | 4/1982 | European Pat. Off. | 623/23 |
| 0220578 | 7/1987 | European Pat. Off. | 623/23 |
| 3132543 | 6/1982 | Fed. Rep. of Germany | 623/23 |

Primary Examiner—David J. Isabella
Attorney, Agent, or Firm—John R. Merkling

[57] ABSTRACT

A prosthesis having a proximal portion of a stem formed as a wedge having opposed tapers such that prostheses can be thrust into a medullary canal and achieve fixation without unduly stressing the cortical bone remaining in the femur. Ribs secure the prosthesis against medial-lateral motion. Simultaneously, a degree of flexibility is provided in an anterior-posterior direction. A slotted distal portion of the stem is flared to enhance fixation distally.

12 Claims, 3 Drawing Sheets

FEMORAL PROSTHESIS WITH WEDGE HAVING OPPOSED TAPERS

BACKGROUND OF THE INVENTION

Our invention relates to femoral prostheses and in particular to prostheses adapted for non-cemented fixation in the medullary canal of a femur.

Various types of femoral prostheses are known and are used for surgical reconstruction of a femur. In general, these prostheses comprise a ball-shaped head mounted at an anatomical angle on a shank. The shank can be thrust into a medullary canal of a femur to mount the prosthesis on a resected surface of the femur. Various means of fixation are known, including bone cement, or porous areas on the prosthesis which promote bony ingrowth, or shoulders proximal to the head for preventing the prosthesis from wedging into the medullary canal.

In femoral prostheses which are particularly adapted for non-cemented applications, initial fixation and subsequent bony ingrowth are important features. Micromotion of the prosthesis may result in reduced fixation, compromising the long-term stability of the prosthesis. At the same time, variation in human anatomy makes it difficult to provide a wide range of tightly fitting sizes for femoral prostheses. Thus, there remains a continuing need for improvement in the design of non-cemented prostheses which provide for firm initial fixation while simultaneously avoiding the possibility of overloading the surrounding bone.

SUMMARY OF OUR INVENTION

Our invention relates to prostheses which are particularly adapted for non-cemented fixation. We have designed a prosthesis having a proximal portion of a stem formed as a wedge having opposed tapers. This structure will be more fully explained below. The result of the opposed tapers is that prostheses can be thrust into a medullary canal and achieve fixation without unduly stressing the cortical bone remaining in the femur. In addition, we have designed a prosthesis having a distal portion of the stem adapted for initial fixation. We have provided ribs which secure the prosthesis against medial-lateral motion. Simultaneously, a degree of flexibility is provided in an anterior-posterior direction to remove or to diminish stress pain. We propose a slight but significant flair in a slotted distal portion of the stem to enhance fixation distally. To resist motion in the anterior-posterior direction, we have provided four areas on the lateral side with different fixation characteristics: A porous area proximally for long-term fixation; a ribbed bone for immediate rigid fixation, a zone with a chamfered rib for intermediate fixation; and a distal zone with a medial-lateral slot which is relatively flexible. To resist motion in the medial-lateral direction, we have provided three areas on the anterior and posterior sides with different fixation characteristics: A porous area proximally which includes the wedge structure for immedate fixation; an intermedaiate portion; and a distal portion with ribs which are increasingly prominent distally.

It is an object of our invention, therefore, to provide a femoral prosthesis with structure which enhances non-cemented fixation.

It is another important object of our invention to provided such a prosthesis with features which reduce stresses in proximal cortical bone.

Another important object of our invention is to provide a femoral prosthesis having distal fixation.

It is yet a further object of our invention to provide a prosthesis with distal fixation which is enhanced in the medial-lateral plane.

A further object of our invention is to provided a prosthesis with flexibility in the anterior-posterior plane combined with distal fixation.

These and other objects and advantages of our invention would be apparent from the following detailed description taken in conjunction with the accompanying drawings.

DETAILED DESCRIPTION OF OUR PREFERRED EMBODIMENT

Figures 1, 2, 3:
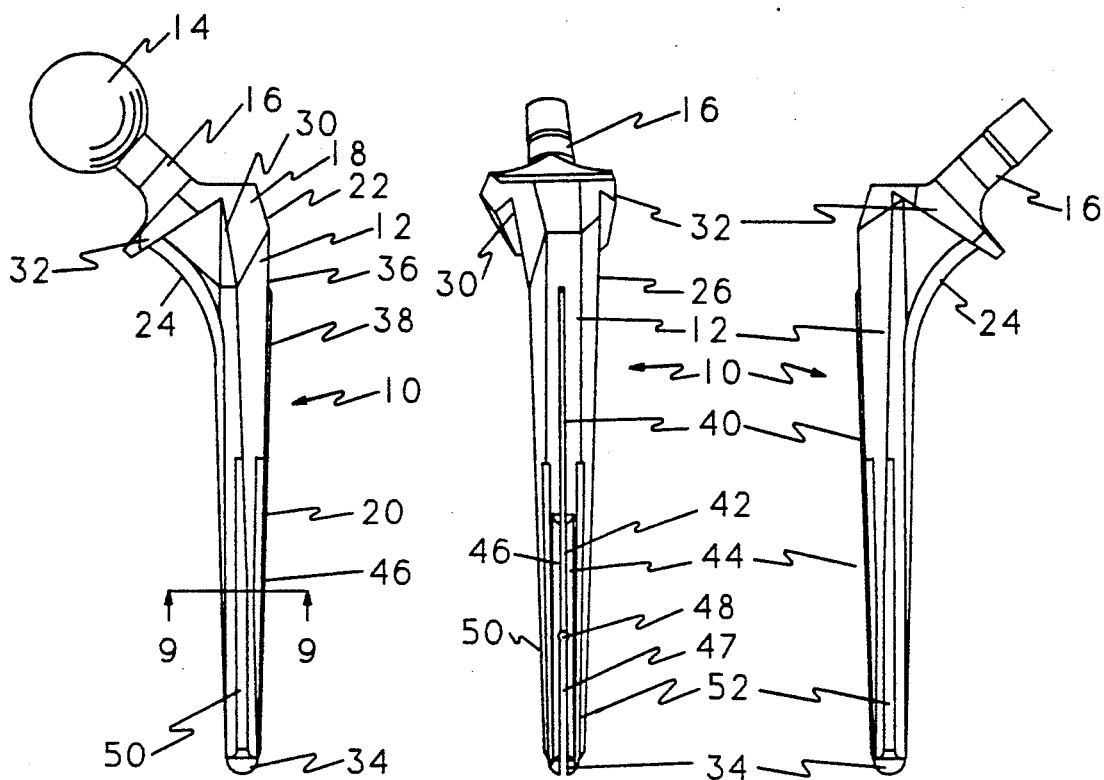
FIG. 1 is a plan view of a femoral prosthesis according to our present invention, with attached femoral head.
FIG. 2 is lateral plan view of the prosthesis stem of FIG. 1.
FIG. 3 is an posterior plan view of the stem of FIG. 1.

In referring to the accompanying drawings, like numerals will refer to like parts throughout the description. In FIG. 1, a femoral prosthesis 10 is illustrated. The femoral prosthesis 10 comprises a stem 12 adapted to be inserted into the medullary canal of a resected femur and a spherical articulating head 14 mounted detachably on a neck 16. The stem 12 has a proximal body portion 18 and a distal portion 20. The distal portion is relatively straight on a lateral side 36 with a slight chamfer 22 proximally. Medially, the proximal portion is concave curved 24. Viewed laterally, as in FIG. 2, an anterior side 28 and posterior side 26 are slightly flared proximally. In addition, on the anterior proximal side, there is a double wedge structure 30 which will be more fully described below. Between the proximal portion and the neck 16, there is a collar 32 which extends anteriorly, medially and posteriorly from the proximal portion.

The distal portion 20 of the stem is relatively straight, but is slightly tapered inwardly from the proximal portion to a distal end 34. On the lateral side 36, we have provided a rib 38 which extends near the double wedge 30 to the distal tip 34. In a proximal half 40 of this ridge 38, which comprises a first zone, the ridge is of relatively rectangular cross-section, providing sharp edges which could grip surrounding cancellous bone. In a distal part 42 of the ridge, we have provided anterior and posterior chamfers, 46, 44 respectively. These chamfers flare out from the ridge 40, widening the ridge and softening its outline. This tends to fill more of the distal meduallary canal but reduces resistance to motion in the anterior-posterior plane in a second zone. In addition, we have provided a slot 47 which extends in the medial-lateral plane from the distal end 34 about half of the distance from the distal end 34 to the beginning of the chambers 44, 46, which comprises a distal zone. The slot 47 terminates at a stress relief bore 48. The slot 47 permits increased flexing of the prosthesis in anterior and posterior directions, reducing point pains which are frequently experienced by patients with femoral prostheses.

On both the anterior and posterior sides 28, 26, in the distal portion of the stem, we have provided ribs 50, 52 with substantially rectangular cross-sections extending from distal tip 34 approximately half of the extent of the stem from the distal tip to the collar 32. The ribs 50, 52 blend into the stem 12 at their proximal ends. They are, therefore, most prominent distally and become flatter proximally.

Figure 9:
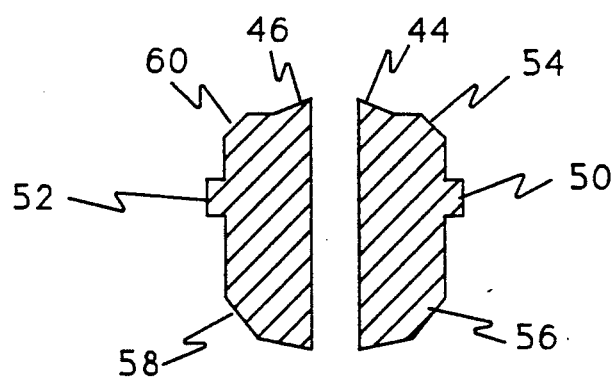
FIG. 9 is a cross-section of a distal portion of the stem of FIG. 1 taken along line 9—9.

As can be seen in FIG. 9, corners of the distal portion of the stem have chamfers 54, 56, 58 and 60 which generally round the outline of the stem, but which still provide relatively sharp corners which will cut into surrounding cancellous bone as the stem is inserted into the medullary canal. The chamfers 44, 46 on the lateral rib 38 can also be seen in the cross-section of FIG. 9.

Figure 4:
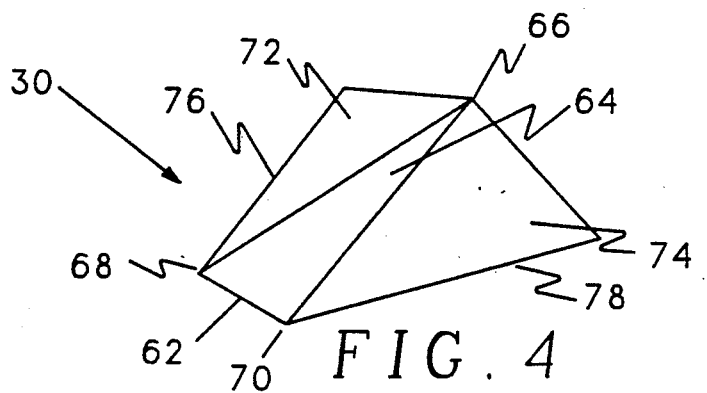
FIG. 4 is a prospective view of a double wedge of the proximal portion of the stem of FIG. 1.
Figure 5:
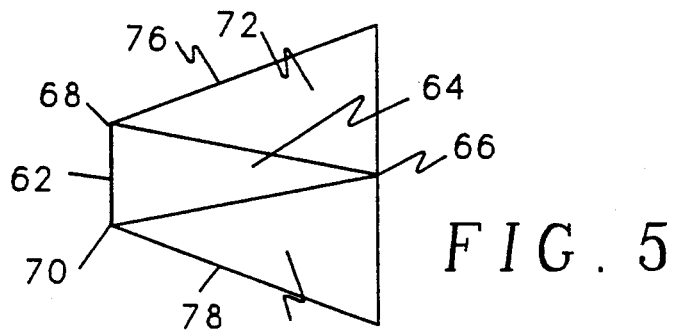
FIG. 5 is a top plan view of the wedge of FIG. 4.
Figure 6:
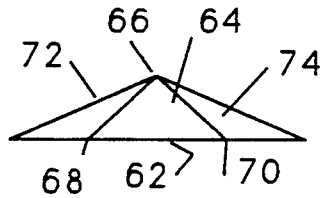
FIG. 6 is a left side plan view of the wedge of FIG. 4.
Figure 7:
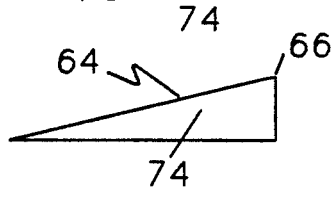
FIG. 7 is a front plan view of the wedge of FIG. 4.
Figure 8:
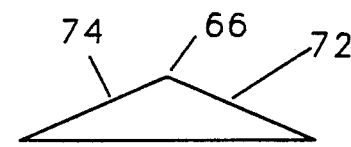
FIG. 8 is a right plan view of the wedge of FIG. 4.

We will now describe in detail the double wedge feature of the proximal portion of our stem. An abstract figure of the double wedge 30 can be seen in FIGS. 4 through 8. The double wedge, as seen in FIG. 4, presents a wide distal blade 62 which is the distal extent of the double wedge feature. The distal blade 62 begins a plane 64 of a first wedge or taper which extends proximally and inclines away from the body of the proximal portion of the stem. The plane 64 terminates at a vertex 66. The plane 64 also defines a second wedge or taper which is broad distally at the blade 62 and narrow proximally at the vertex 66. The edge 62 terminates at a medial vertex 68 and a lateral vertex 70. These vertices 68, 70 are also vertices of similar inclined wedge planes, a medial wedge plane 72 and a lateral wedge plane 74. Each of these planes 72, 74 intersect at the proximal vertex 66. A medial edge 76 of the medial wedge plane 72 and a lateral edge 78 of the lateral wedge plane 74 flare away from each other from their respective vertices 68, 70 from distal to proximal location. The medial edge 76 and lateral edge 78 define a third taper which is broader proximally than it is distally. This structure, which can also be seen in plan view in FIGS. 5, 6, 7, and 8, creates opposed wedges.

As the stem of the prosthesis is thrust into the medullary canal, the distal edge 62 will first encounter bone. As the beginning of a wedge, this edge is wide and does not rapidly increase the stress in surrounding cortical bone. As the stem is thrust further into the medullary canal and the bone progresses from the edge 62 toward the vertex 66, the wedge plane 64 will press further and further into the surrounding cancellous and cortical bone, increasing fixation. At the same time, the width of this wedge plane 64 will decrease, allowing the stresses to diminish. Simultaneously, the flared features of the medial and lateral wedge planes 72, 74 will tend to fill more of the medullary canal.

Figure 13:
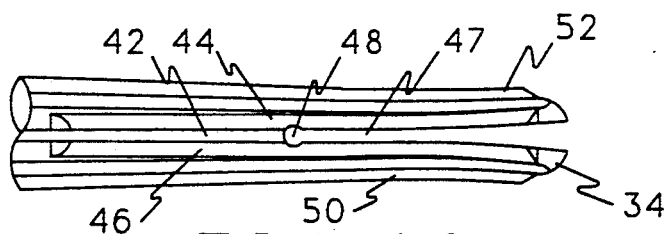
FIG. 13 is an enlarged partial plan view of the stem of FIG. 2, showing a flared distal slot.

Before applying porous coating to the proximal portion of the stem, we force open the slot 46 as seen in FIG. 13. The slot itself is on the order of 3 plus or minus 1 millimeters wide. with the additional flair, the ends of the prosthesis are displaced away from each other an additional 3 plus or minus 1 millimeters. This is in effect a spring at the distal end of the prosthesis, which more completely fills the medullary canal. When the prosthesis is heated in connection with the process of applying a porous coating, stresses from flaring the slot will be relieved and the flair set. We anticipate that the slot will not be compressed beyond the original dimensions of the slot when inserted. There will be variability because of the flair, but there should always be a gap at the distal end of the stem when the prosthesis is correctly implanted.

Figures 10, 11, 12:
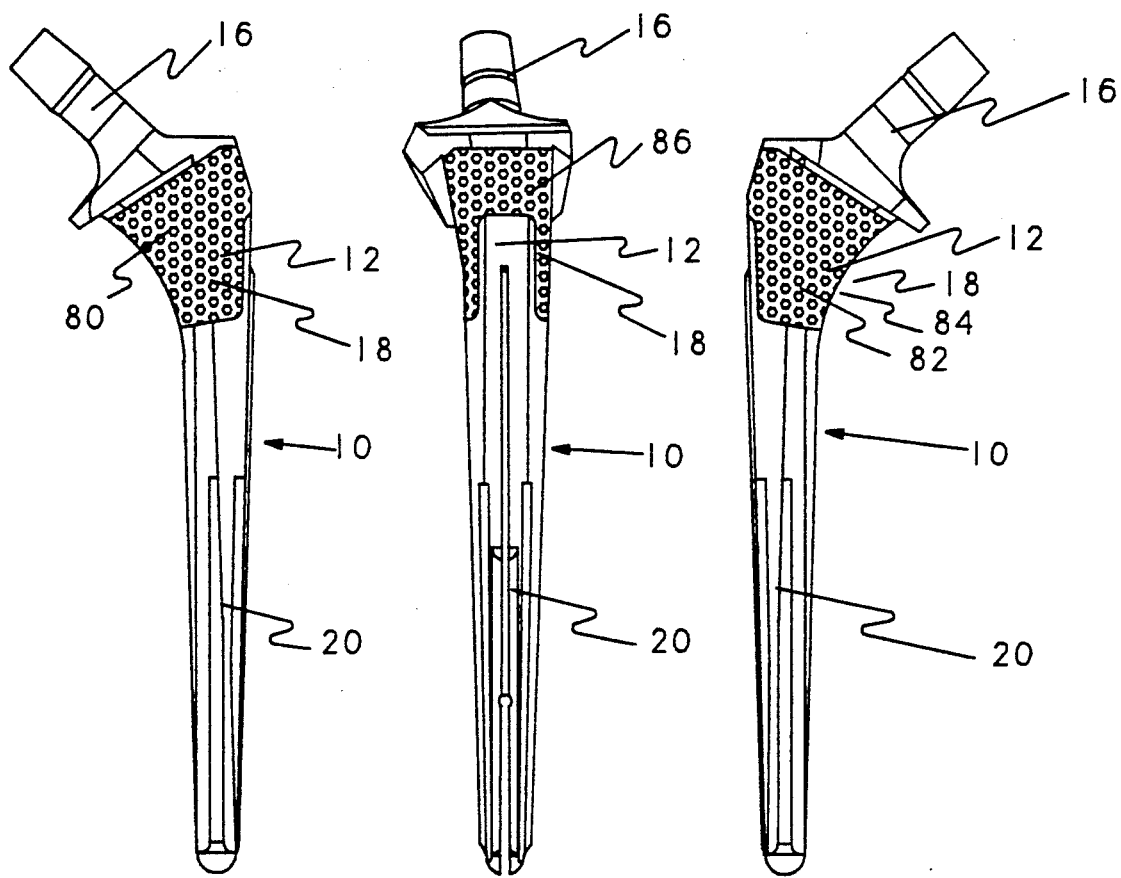
FIG. 10 is anterior plan view of the stem of FIG. 1 showing our preferred location for porous coating.
FIG. 11 is a lateral plan view of the stem of FIG. 10.
FIG. 12 is an posterior plan view of the stem of FIG. 10.

FIGS. 10, 11 and 12 illustrate the location of porous areas provided in our prosthesis. Although preferably comprised of porous titanium, these areas define a geometry more clearly seen in FIGS. 1, 2 and 3 and described above. A proximal porous portion 80 for the anterior side, seen in FIG. 10, would therefore, have the opposed wedge geometry described above. The proximal posterior porous area 82, seen in FIG. 12, would be of approximately equal area to the portion 80 but, in our preferred embodiment, would not have the opposed wedge configuration, although such a structure could be provided without departing from the teachings of our invention. A porous zone 84 is also provided medially, as is a porous zone 86 on the lateral side of our prosthesis. The porous portions 80, 82 and zones 84, 86 provide long-term proximal fixation as surrounding bone heals into the porous material.

It will be apparent from the foregoing description that our prosthesis provides different fixation characteristics in both the anterior-posterior and the medial-lateral direction, using various portions and zones along the length of the prosthesis. To resist motion in the anterior-posterior direction, we have described four areas or zones, principally on the lateral side. Proximally, there is a porous zone which provides long-term fixation. In a first intermediate zone, a prominent ridge provides immediate rigid fixation. In the second, more distal, intermediate zone, the ridge is chamfered and more motion is possible, although there is substantial resistance to motion. In a distal zone, the chamfered ridge coupled with the slot allows more motion and decreases point stress. To resist motion in the medial-lateral direction, we have described a proximal portion which has the characteristics of both a porous area for long-term fixation and an opposed wedge for immediate fixation without unduly high stress. An intermediate portion separates this proximal porous portion from a distal portion. In the distal portion, the ribs taper, becoming increasingly prominent distally, thereby providing an increased resistance to medial-lateral motion towards the distal end of the prosthesis.

Our invention may be embodied in other specific forms without departing from the spirit or essential characteristics thereof. The present embodiment is therefore considered in all aspects as illustrative and not restrictive, the scope of our invention being indicated by the appended claims rather than by the foregoing description, and all changes which come within the meaning and range of equivalency of the claims are therefore intended to be embraced therein.

We claim as our invention:

1. An implantable prosthesis comprising articulating head; and
   a stem connected to said head for mounting said prosthesis on a bone of a patient, said stem having integrally fixed on at least one side thereof
   a bone engaging wedge structure having opposed tapers, said wedge structure having a first tapered surface commencing adjacent said side distally and rising away from said side proximally and which is broad distally and narrow proximally, said surface lying generally adjacent bone when said prosthesis is implanted.

2. The implantable prosthesis according to claim 1 wherein the wedge structure further comprises
   a second tapered surface between said first tapered surface and said side of said stem, said second tapered surface forming a first junction between said second surface and said side and
   a third tapered surface between said first tapered surface and said side of said stem, said third tapered surface forming a second junction between said third tapered surface and said side, said first and second junctions being spaced apart from each other a distal distance at least the distal breadth of said first surface and a proximal distance greater than said distal distance.

3. The implantable prosthesis according to claim 2 wherein said first tapered surface is a plane.

4. The implantable prosthesis according to claim 3 wherein said second and third tapered surfaces are planes.

5. The implantable prosthesis according to claim 4, said stem further comprising
   means for resisting motion in anterior-posterior directions, said means comprising
      porous fixation means in a first proximal zone on the stem;
      means for providing immediate, substantially rigid fixation in a first intermediate zone on the stem, substantially adjacent said proximal zone;
      means for providing immediate, moderate fixation in a second intermediate zone on the stem, substantially adjacent distally from said first intermediate zone; and
      means for providing immediate, anteriorly-posteriorly flexible fixation in a distal zone on the stem.

6. The implantable prosthesis according to claim 5 wherein the rigid fixation means comprise a ridge extending from a proximal end to a distal end of said first intermediate zone.

7. The implantable prosthesis according to claim 6 wherein the moderate fixation means comprise chamfered anterior and posterior edges on said ridge, said ridge and said edges extending from a proximal end to a distal end of said second intermediate zone.

8. The implantable prosthesis according to claim 7 wherein the flexible fixation means comprise a slot extending in a medial-lateral plane in said distal zone.

9. The implantable prosthesis according to claim 8 wherein the slot is flared.

10. The implantable prosthesis according to claim 9 wherein the means for resisting motion in anterior-posterior directions is on a lateral side of said stem.

11. The implantable prosthesis according to claim 10 said stem further comprising
    means for resisting motion in medial-lateral directions, said means comprising
    porous fixation means in a second proximal zone on the stem;
    immediate fixation means in a zone on the stem distal from said second proximal zone, said immediate fixation means providing increasing resistance to medial-lateral motion from a proximal end of said distal zone to a distal end of said distal zone.

12. The implantable prosthesis according to claim 11 wherein the immediate fixation means comprise a ridge tapering from said proximal end of said distal zone to said distal end of said distal zone.

* * * * *